United States Patent
Hernandez

(10) Patent No.: US 9,138,220 B2
(45) Date of Patent: Sep. 22, 2015

(54) KNOTLESS SUTURE ANCHOR

(75) Inventor: Joseph Hernandez, Sandwich, MA (US)

(73) Assignee: MEDOS INTERNATIONAL SARL, Le Locle (CH)

( * ) Notice: Subject to any disclaimer, the term of this patent is extended or adjusted under 35 U.S.C. 154(b) by 376 days.

(21) Appl. No.: 13/329,836

(22) Filed: Dec. 19, 2011

(65) Prior Publication Data
US 2013/0158597 A1  Jun. 20, 2013

(51) Int. Cl.
*A61B 17/04* (2006.01)

(52) U.S. Cl.
CPC ....... *A61B 17/0401* (2013.01); *A61B 2017/045* (2013.01); *A61B 2017/0409* (2013.01); *A61B 2017/0424* (2013.01); *A61B 2017/0441* (2013.01); *A61B 2017/0445* (2013.01); *A61B 2017/0446* (2013.01); *A61B 2017/0448* (2013.01); *A61B 2017/0451* (2013.01)

(58) Field of Classification Search
CPC .......... A61B 17/0401; A61B 2017/0409; A61B 2017/0412; A61B 2017/0414; A61B 2017/042; A61B 2017/0422; A61B 2017/0424; A61B 2017/0425; A61B 2017/0427; A61B 2017/043; A61B 2017/0432; A61B 2017/0433; A61B 2017/044; A61B 2017/0445; A61B 2017/0446; A61B 2017/0448; A61B 2017/045; A61B 2017/0454; A61B 2017/0456; A61B 2017/0459; A61B 17/0487; A61F 2002/0823; A61F 2002/0829; A61F 2002/0835; A61F 2/0811
USPC ......... 606/232, 144, 148, 151, 224, 225, 228, 606/233, 79, 80, 96, 104
See application file for complete search history.

(56) References Cited

U.S. PATENT DOCUMENTS

| | | | | | |
|---|---|---|---|---|---|
| 5,464,427 | A | * | 11/1995 | Curtis et al. | 606/232 |
| 5,480,403 | A | * | 1/1996 | Lee et al. | 606/232 |
| 5,643,321 | A | * | 7/1997 | McDevitt | 606/232 |
| 5,649,963 | A | * | 7/1997 | McDevitt | 606/232 |
| 5,702,397 | A | * | 12/1997 | Goble et al. | 606/232 |
| 5,814,071 | A | * | 9/1998 | McDevitt et al. | 606/232 |
| 5,899,921 | A | * | 5/1999 | Caspari et al. | 606/232 |
| RE36,289 | E | * | 8/1999 | Le et al. | 606/232 |
| 5,935,129 | A | * | 8/1999 | McDevitt et al. | 606/232 |

(Continued)

FOREIGN PATENT DOCUMENTS

WO   WO 9838938 A1 *  9/1998  ............. A61B 17/68
WO   WO-2007146338 A2   12/2007

OTHER PUBLICATIONS

"PushLock® Knotless Anchor for Bankart & SLAP Repair Surgical Technique" Arthrex Brochure, 2008.

(Continued)

*Primary Examiner* — Katherine Rodjom
*Assistant Examiner* — Erin Colello

(57) ABSTRACT

Methods and devices are provided for anchoring suture to bone. In one exemplary embodiment, a suture anchor is provided that includes a proximal component, a distal component, and an intermediate component positioned between the distal component and the proximal component. The proximal and distal components can each be configured to move independent of one another and to move relative to the intermediate component. In this way, the proximal, intermediate, and distal components of the suture anchor can be configured to cooperate with one another to prevent removal of the suture anchor from a bone hole in which the suture anchor is disposed and to lock a suture relative to the suture anchor and to the bone hole.

25 Claims, 11 Drawing Sheets

(56) References Cited

U.S. PATENT DOCUMENTS

| | | | |
|---|---|---|---|
| 5,957,953 A * | 9/1999 | DiPoto et al. | 606/232 |
| 6,074,403 A | 6/2000 | Nord | |
| 6,162,234 A * | 12/2000 | Freedland et al. | 606/151 |
| 6,214,050 B1 * | 4/2001 | Huene | 623/17.15 |
| 6,585,730 B1 | 7/2003 | Foerster | |
| 6,673,094 B1 * | 1/2004 | McDevitt et al. | 606/232 |
| 6,716,234 B2 | 4/2004 | Grafton et al. | |
| 6,846,313 B1 * | 1/2005 | Rogers et al. | 606/326 |
| 6,932,834 B2 * | 8/2005 | Lizardi et al. | 606/232 |
| 6,991,636 B2 | 1/2006 | Rose | |
| 7,201,754 B2 * | 4/2007 | Stewart et al. | 606/328 |
| 7,329,272 B2 | 2/2008 | Burkhart et al. | |
| 7,517,357 B2 * | 4/2009 | Abrams et al. | 606/232 |
| 7,585,311 B2 | 9/2009 | Green et al. | |
| 7,588,587 B2 * | 9/2009 | Barbieri et al. | 606/232 |
| 7,828,820 B2 * | 11/2010 | Stone et al. | 606/232 |
| 7,867,264 B2 * | 1/2011 | McDevitt et al. | 606/313 |
| 7,896,907 B2 * | 3/2011 | McDevitt et al. | 606/304 |
| 8,409,252 B2 * | 4/2013 | Lombardo et al. | 606/232 |
| 8,672,970 B2 * | 3/2014 | Ferragamo et al. | 606/232 |
| 2002/0095180 A1 | 7/2002 | West et al. | 606/228 |
| 2003/0144667 A1 * | 7/2003 | Enayati | 606/72 |
| 2003/0149448 A1 | 8/2003 | Foerster et al. | |
| 2003/0187444 A1 * | 10/2003 | Overaker et al. | 606/72 |
| 2004/0138706 A1 * | 7/2004 | Abrams et al. | 606/232 |
| 2004/0249466 A1 * | 12/2004 | Liu et al. | 623/17.16 |
| 2006/0235413 A1 * | 10/2006 | Denham et al. | 606/72 |
| 2006/0271060 A1 | 11/2006 | Gordon | |
| 2006/0282081 A1 * | 12/2006 | Fanton et al. | 606/72 |
| 2007/0219557 A1 | 9/2007 | Bourque et al. | |
| 2007/0225719 A1 | 9/2007 | Stone et al. | |
| 2008/0009904 A1 | 1/2008 | Bourque et al. | |
| 2008/0033460 A1 | 2/2008 | Ziniti et al. | |
| 2008/0033486 A1 | 2/2008 | Whittaker et al. | |
| 2008/0051836 A1 * | 2/2008 | Foerster et al. | 606/232 |
| 2008/0086138 A1 * | 4/2008 | Stone et al. | 606/72 |
| 2008/0147119 A1 * | 6/2008 | Cauldwell et al. | 606/232 |
| 2008/0161864 A1 * | 7/2008 | Beck et al. | 606/326 |
| 2009/0088798 A1 | 4/2009 | Snyder et al. | |
| 2009/0149883 A1 * | 6/2009 | Brunsvold | 606/232 |
| 2009/0157124 A1 | 6/2009 | Ferragamo et al. | |
| 2009/0187216 A1 | 7/2009 | Schmieding et al. | |
| 2009/0248068 A1 * | 10/2009 | Lombardo et al. | 606/232 |
| 2010/0198258 A1 * | 8/2010 | Heaven et al. | 606/232 |
| 2010/0292732 A1 * | 11/2010 | Hirotsuka et al. | 606/232 |
| 2010/0331881 A1 * | 12/2010 | Hart | 606/232 |
| 2011/0152929 A1 | 6/2011 | McDevitt et al. | |
| 2011/0264140 A1 * | 10/2011 | Lizardi et al. | 606/232 |

OTHER PUBLICATIONS

"Swivelock® Anchor System: The Knotless Surgical Technique for Ligament Reconstruction" Arthrex Vet Systems Brochure, 2010.

"Versalok™ Surgical Technique for Rotator Cuff Repair" DePuy Mitek Brochure, 2007.

Partial European Search Report issued in European Application No. 12197867.0 dated Sep. 4, 2014.

* cited by examiner

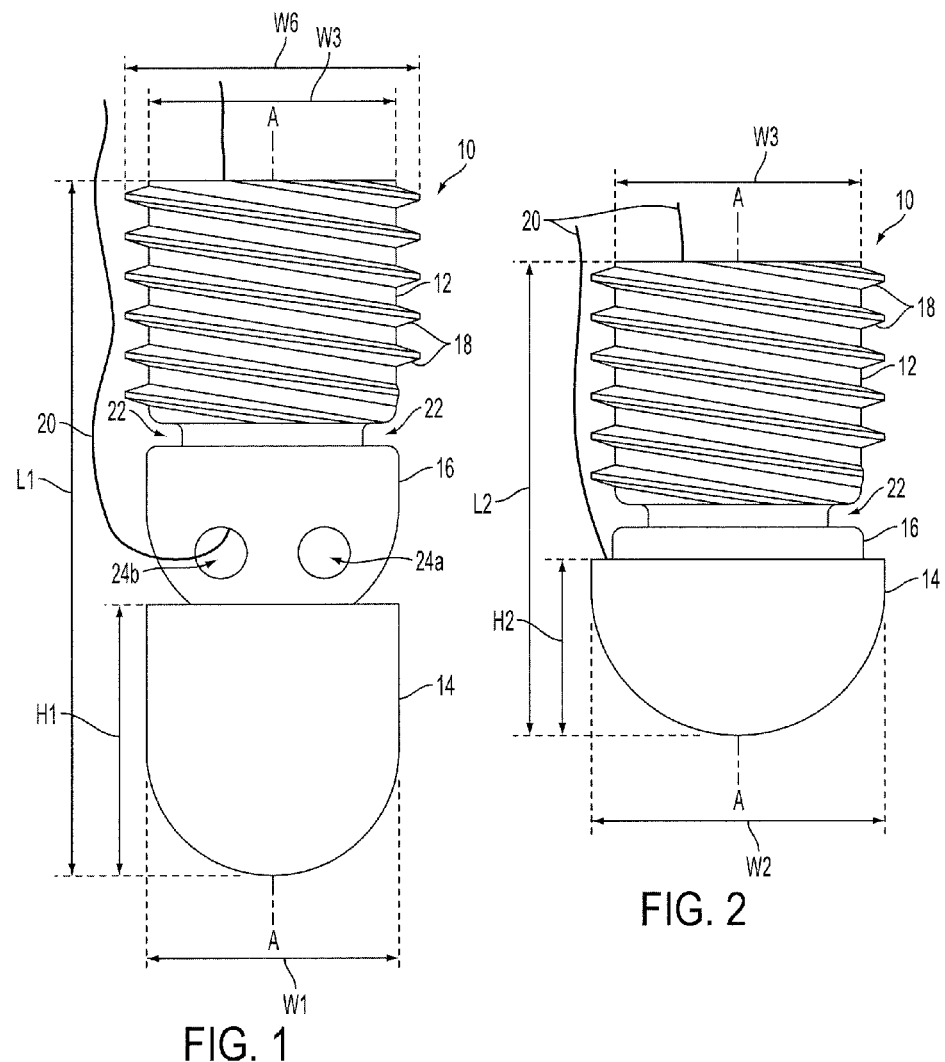

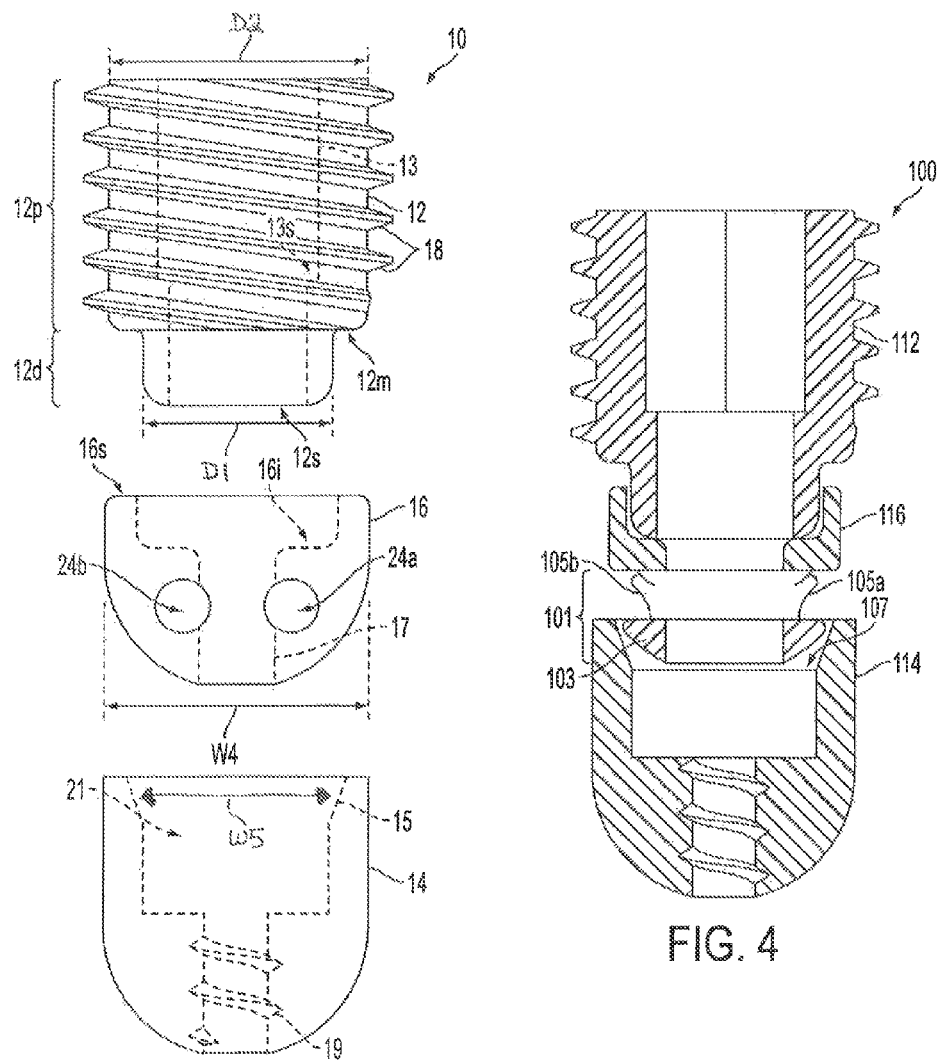

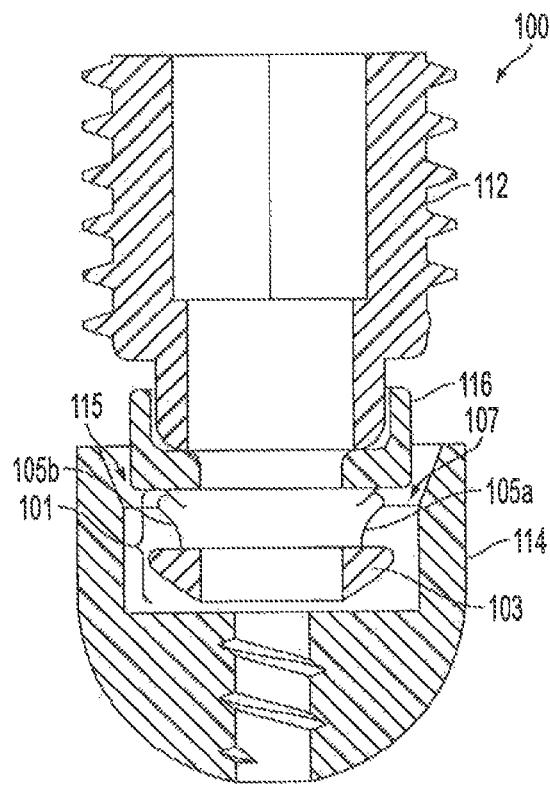
FIG. 5
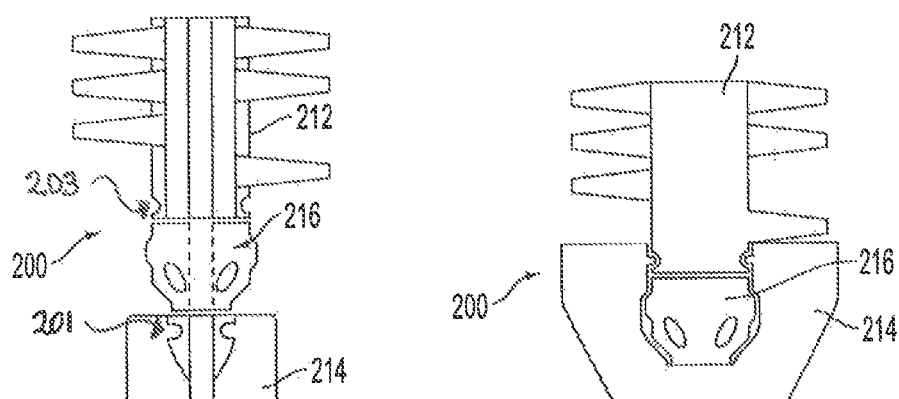
FIG. 6
FIG. 7

KNOTLESS SUTURE ANCHOR

FIELD OF THE INVENTION

The present invention relates generally to methods and devices for anchoring soft tissue to bone, and in particular to knotless suture anchors and methods for use.

BACKGROUND OF THE INVENTION

The complete or partial detachment of ligaments, tendons, and/or other soft tissues from their associated bones within the body are relatively commonplace injuries, particularly among athletes. Such injuries are generally the result of excessive stresses being placed on these tissues. By way of example, tissue detachment may occur as the result of an accident such as a fall, over-exertion during a work-related activity, during the course of an athletic event, or in any one of many other situations and/or activities.

In the case of a partial detachment, the injury will frequently heal itself, if given sufficient time and if care is taken not to expose the injury to further undue stress. In the case of complete detachment, however, surgery may be needed to re-attach the soft tissue to its associated bone or bones. Numerous devices are currently available to re-attach soft tissue to bone. Examples of such currently-available devices include screws, staples, suture anchors and tacks. In soft tissue re-attachment procedures utilizing screws, the detached soft tissue is typically moved back into its original position over the bone. Then the screw is screwed through the soft tissue and into the bone, with the shank and head of the screw holding the soft tissue to the bone. Similarly, in soft tissue re-attachment procedures utilizing staples, the detached soft tissue is typically moved back into its original position over the bone. Then the staple is driven through the soft tissue and into the bone, with the legs and bridge of the staple holding the soft tissue to the bone.

In soft tissue re-attachment procedures utilizing suture anchors, an anchor-receiving hole is generally first drilled in the bone at the desired point of tissue re-attachment. Then a suture anchor is deployed in the hole using an appropriate installation tool. This effectively locks the suture to the bone, with the free end(s) of the suture extending out of the bone. The free ends of the suture are passed through or around the soft tissue and are used to tie the soft tissue securely to the bone.

While current suture anchors are effective in anchoring soft tissue to bone, one drawback with current devices is that anchors can shift within bone following implantation due to a problem such as poor bone quality of a particular patient. The anchor and/or any soft tissue attached to the anchor via suture can therefore shift in position relative to the bone, which can delay or prevent proper healing.

Accordingly, there remains a need for improved methods and devices for attaching soft tissue to bone.

SUMMARY OF THE INVENTION

In one embodiment, a suture anchor is provided that includes a cannulated elongate member including a distal component, a proximal component, and an intermediate component positioned between the distal component and the proximal component. The cannulated elongate member can be configured to be secured within a bone hole by a threaded engagement between the proximal component and the bone hole, and by radial expansion of the distal component within the bone hole. The cannulated elongate member can be configured to secure a suture thereto by engaging the suture between the bone hole and threads formed on an external surface of the proximal component, and by engaging the suture between the distal component and the intermediate component. The proximal, intermediate, and distal components can be axially aligned.

The proximal, intermediate, and distal components can each have a variety of configurations. The proximal component can be configured to rotate about a longitudinal axis thereof relative to the intermediate and distal components. The distal component can be configured to radially expand and engage the suture between the distal component and the intermediate component when the intermediate component is inserted into a bore formed in the distal component. The intermediate component can have a hole formed through a sidewall thereof proximal to a distal end of the intermediate component and proximal to a proximal end of the distal component. The hole can be configured to have the suture extend therethrough at least when the suture is engaged between the distal component and the intermediate component. The intermediate and distal components can have unthreaded external surfaces.

In another embodiment, a suture anchor is provided that includes a cannulated elongate member including a distal component, a proximal component, and an intermediate component positioned between the distal component and the proximal component. When the cannulated elongate member is disposed within a bone hole and a suture is coupled to the cannulated elongate member, the cannulated elongate member can be configured to have a first configuration and a second configuration. In the first configuration, the proximal component can be threadably engaged with the bone hole to prevent removal of the cannulated elongate member from the bone hole, and the suture can be engaged between the bone hole and threads on an external surface of the proximal component. The suture can be freely slidable through the intermediate component. In the second configuration, the distal component can be advanced proximally over the intermediate component such that the distal component radially expands, as compared to the distal component in the first configuration, to engage the bone hole. The suture can be engaged between the distal component and the intermediate component.

When the cannulated elongate member is in the first configuration, a first length of the intermediate component can be disposed within the distal component, and when the cannulated elongate member is in the second configuration, a second length of the intermediate component can be disposed within the distal component. The second length can be greater than the first length. When the cannulated elongate member is in the second configuration, the proximal component can be threadably engaged with the bone hole to prevent removal of the cannulated elongate member from the bone hole, and/or the suture can not be freely slidable through the intermediate component.

In another aspect, a suture anchoring system is provided that includes an elongate shaft having a proximal handle portion and a distal portion configured to be inserted through tissue, a proximal component freely slidably disposed on the distal portion of the elongate shaft and having threads formed on an external surface thereof, an intermediate component freely slidably disposed on the distal portion of the elongate shaft at a location distal to the proximal component, and a distal component threadably engaged with threads formed on the distal portion of the elongate shaft. The distal component can be positioned distal to the intermediate component, and the distal component can be configured to expand when the distal component is advanced over the intermediate component.

The proximal, intermediate, and distal components can each have a variety of configurations. The distal and intermediate components can be configured to engage a suture therebetween when the distal component is advanced over the intermediate component.

The elongate shaft can also have a variety of configurations. The elongate shaft can extend through axially aligned inner lumens formed through the proximal, intermediate, and distal components. The elongate shaft can be configured to move proximally relative to the proximal and intermediate components to advance the distal component proximally relative to the proximal and intermediate components such that the distal component expands around the intermediate component. The elongate shaft can be configured to be threadably disengaged from the distal component after the distal component has radially expanded around the intermediate component to allow the elongate shaft to be slidably released from the proximal, intermediate, and distal components.

In yet another aspect, a method for anchoring tissue to bone is provided that includes advancing a suture anchor disposed on a distal end of an insertion shaft into bone distally such that the suture anchor is at least partially disposed within the bone, threads on a proximal portion of the suture anchor are engaged with the bone, and a suture coupled to soft tissue is engaged between an outer surface of the suture anchor and the bone. After advancing the suture anchor into the bone, the suture anchor can be actuated to cause a sleeve of the suture anchor to expand to engage the bone and prevent removal of the suture anchor from the bone, and to cause the suture to be engaged by compression fit between the sleeve and a pin member of the suture anchor. Advancing the suture anchor can include rotating the insertion shaft and the proximal portion of the suture anchor relative to the pin member and the sleeve. In some embodiments, the insertion shaft can include a bone-penetrating distal tip, and advancing the suture anchor can include forming a hole in the bone. In some embodiments, advancing the suture anchor can include positioning the suture anchor into a pre-formed hole in the bone.

Actuating the suture anchor can include advancing the insertion shaft proximally such that the sleeve moves proximally relative to the pin member and the proximal portion of the suture anchor. Advancing the insertion shaft proximally can include pulling the insertion shaft in a proximal direction.

When the suture anchor is advanced into the bone and when the suture anchor is actuated, the insertion shaft can extend through axially aligned inner lumens formed through the proximal portion, the sleeve, and the pin member. The sleeve can be located distal to the proximal portion, and the pin member can be located between the sleeve and the proximal portion.

BRIEF DESCRIPTION OF THE DRAWINGS

The invention will be more fully understood from the following detailed description taken in conjunction with the accompanying drawings, in which:

FIG. 1 is a side view of one embodiment of a suture anchor in an undeployed configuration;

FIG. 2 is a side view of the suture anchor of FIG. 1 in a deployed configuration;

FIG. 3 is an exploded, partially transparent view of the suture anchor of FIG. 1;

FIG. 4 is side, cross-sectional view of another embodiment of a suture anchor in an undeployed configuration;

FIG. 5 is a side, cross-sectional view of the suture anchor of FIG. 4 in a deployed configuration;

FIG. 6 is a side, partially transparent view of yet another embodiment of a suture anchor in an undeployed configuration;

FIG. 7 is side view of the suture anchor of FIG. 6 in a deployed configuration;

DETAILED DESCRIPTION OF THE INVENTION

Figure 8:
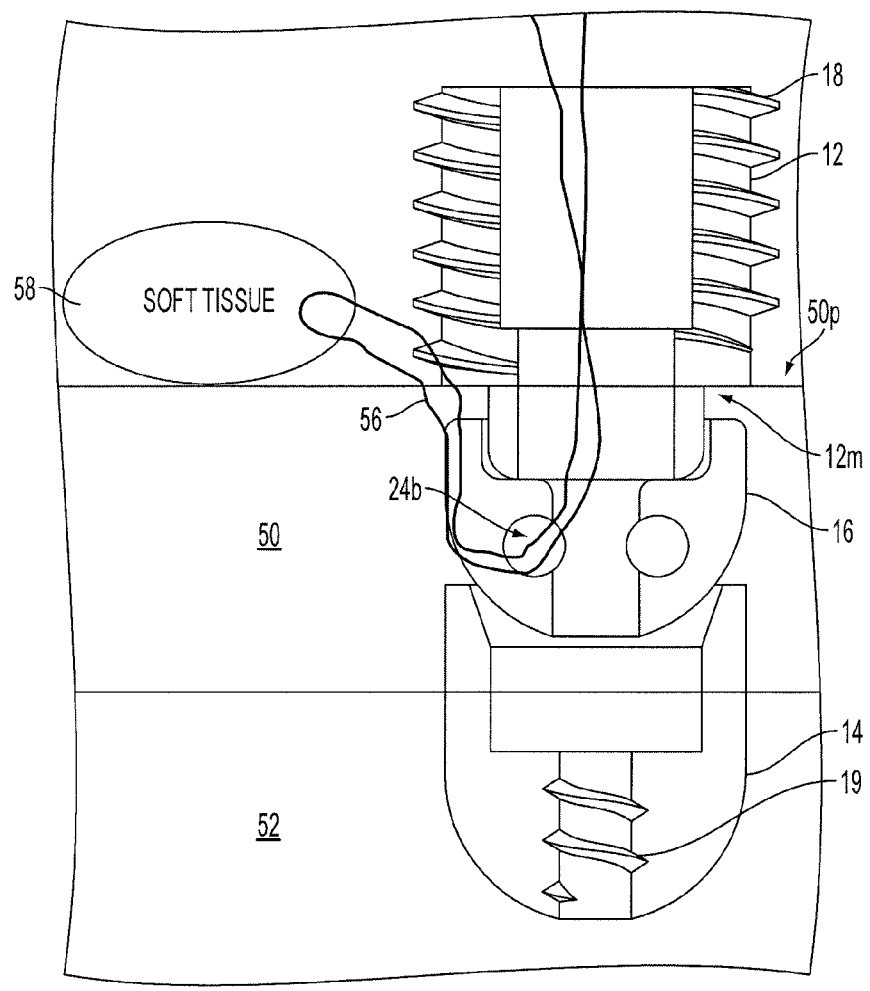
FIG. 8 is a side, cross-sectional view of the suture anchor of FIG. 1 partially disposed in the undeployed configuration in a bone hole.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are provided for anchoring soft tissue to bone. In general, the methods and devices can allow soft tissue to be secured to bone using a suture coupled to a suture anchor without the need to knot or otherwise tie the suture to secure the soft tissue in place relative to the bone. Exemplary suture anchor drivers are also provided that can be used with the various methods and devices disclosed herein, or with other methods and devices known in the art. A person skilled in the art will appreciate that while methods and devices are disclosed herein for anchoring soft tissue to bone, the methods and devices can be used in a variety of other medical procedures for anchoring various objects to one another.

In an exemplary embodiment, a cannulated suture anchor is provided that includes a proximal component, a distal component, and an intermediate component positioned between the distal component and the proximal component. The proximal and distal components can each be configured to move independent of one another and to move relative to the intermediate component. In this way, the proximal, intermediate, and distal components of the suture anchor can be configured to cooperate with one another to prevent removal of the suture anchor from a bone hole in which the suture anchor is disposed and to lock a suture relative to the suture anchor and to the bone hole. The suture can be coupled to the suture anchor and can be configured to be engaged between the bone hole and threads formed on an external surface of the proximal component, as well as engaged between the distal component and the intermediate component. The suture can be attached to a soft tissue, thereby allowing the suture anchor to lock the soft tissue in a fixed position relative to the bone hole to facilitate healing. The suture anchor can therefore be configured to lock the suture and soft tissue relative to the bone hole using two types of fixation, namely by compressing the suture between the bone hole and the external threads of the proximal portion and by compressing the suture between the intermediate and distal components. By being configured to lock the suture and soft tissue relative to the bone hole using two types of fixation, the suture anchor can reduce chances of the suture and/or the soft tissue from slipping or migrating after the suture anchor has been implanted into bone, thereby facilitating healing. Additionally, the suture anchor can be configured to engage the bone hole in two independent ways to prevent removal of the suture anchor therefrom. First, the threads on the proximal portion of the suture anchor can engage the bone hole. Second, the distal component can be configured to radially expand when the intermediate component is inserted into a bore formed in the distal portion, thereby pressing the distal component against the bone hole to secure the anchor therein by compression fit. The suture anchor can therefore help prevent slipping or migration of the suture anchor within the bone hole once implanted therein, thereby facilitating healing.

The suture anchor can be formed from a variety of materials. In an exemplary embodiment, the material can have physical properties that are sufficient to allow a driver to be inserted into a cannulated interior of the anchor and to be used to drive the anchor into bone without damaging the anchor. The properties of the material will depend on the particular configuration of the anchor. Non-limiting examples of materials that can form the suture anchor include metals such as titanium, polymers such as polyether ether ketone (PEEK), and combinations thereof. In an exemplary embodiment, the anchor can be absorbable, but the anchor can instead be non-absorbable, or combinations thereof.

FIGS. 1-3 illustrate one exemplary embodiment of a suture anchor 10 configured to anchor soft tissue to bone. As in the illustrated embodiment, the anchor 10 can be configured as an elongate member including three components. The components can be axially aligned and can include a proximal component 12, a sleeve or distal component 14, and a pin member or intermediate component 16 positioned between the proximal component 12 and the distal component 14. Each of the proximal, distal, and intermediate components 12, 14, 16 can have inner lumens 13, 15, 17 extending therethrough and in communication with one another such that the suture anchor 10 is cannulated. The inner lumens 13, 15, 17 are axially aligned along a longitudinal axis A of the anchor 10 in the illustrated embodiment, but the inner lumens 13, 15, 17 can be radially offset from the longitudinal axis A.

Each of the proximal, distal, and intermediate components 12, 14, 16 can have a variety of sizes, shapes and configurations. As shown in the illustrated embodiment, the anchor 10 can have a substantially cylindrical shape with each of the proximal, distal, and intermediate components 12, 14, 16 having rounded outer surfaces. In this way, the anchor 10 can correspond to a substantially cylindrical shape of a bone hole and be easily and securely disposed therein.

The proximal component 12 can be cannulated, as mentioned above, and can have at least one bone-engaging surface feature formed thereon that is configured to engage bone, e.g., a bone surface of a bone hole. While various surface features can be used, such as teeth, ribs, ridges, barbs, protrusions, etc., as in the illustrated exemplary embodiment, the proximal component 12 can include a surface feature in the form of at least one thread 18 formed on an external surface thereof and extending around the proximal component 12. The thread 18 can be a single, continuous thread as in the illustrated embodiment that extends around the proximal component 12, or the thread 18 can include a plurality of threads, as will be appreciated by a person skilled in the art.

The thread 18 can be located in at least a proximal portion 12p of the proximal component 12. As in the illustrated embodiment, the thread 18 can extend from a proximal end of the proximal component 12 and terminate proximal to a distal end of the proximal component 12, and hence extend along only a proximal portion of the proximal component 12, e.g., terminate proximal to a distal end thereof. The proximal portion 12p of the proximal component 12 can therefore include the thread 18 while a distal portion 12d of the proximal component 12 can be unthreaded and free of bone-engaging surface features. Whether the anchor 10 is in a deployed configuration or an undeployed configuration, discussed further below, the thread 18 can be located proximal to the distal and intermediate components 14, 16, which can help maximize an amount of the thread 18 available to engage bone.

The proximal component 12 can include a reduced outer diameter region in which the proximal component 12 has a smaller outer diameter than a remainder of the proximal component 12. In an exemplary embodiment, a minor outer diameter D1 of the distal portion 12d of the proximal component 12 can be less than an outer diameter D2 of the proximal portion 12p of the proximal component 12. The proximal component 12 can be configured to be inserted into a proximal end of the intermediate component 16 and it can be at least partially disposed within the inner lumen 17 of the intermediate component 16. In an exemplary embodiment, the distal portion 12d of the proximal component 12 can be configured to be at least partially inserted into the intermediate component 16, while the proximal portion 12p of the proximal component 12 can be prevented from being inserted at all into the intermediate component. The thread 18 formed on the proximal portion 12p of the proximal component 12 can therefore be prevented from being inserted into and possibly damaging the intermediate component 16, and a maximum amount of the thread 18 can be available to engage bone.

At least one of the proximal and intermediate components 12, 16 can include a stop mechanism configured to prevent the proximal component 12 from being inserted into the intermediate component 16 beyond a certain amount. As in the illustrated embodiment, and as discussed further below, the intermediate component 16 can include an internal stop surface 16i configured to abut a distal surface 12s of the proximal component 12. In other words, the internal stop surface 16i of the intermediate component 16 and the distal surface 12s of the proximal component 12 can be configured to cooperate as a stop mechanism to prevent over-insertion of the proximal component 12 into the inner lumen 17 of the intermediate component 16. Alternatively or in addition, a distal surface 12m of the proximal portion 12p can be configured to abut a proximal surface 16s of the intermediate component 16 to prevent the proximal component 12 from being inserted into the inner lumen 17 of the intermediate component 16 beyond a certain amount. In other words, the distal surface 12m of the proximal portion 12p and the proximal surface 16s of the intermediate component 16 can be configured to cooperate as a stop mechanism to prevent over-insertion of the proximal component 12 into the intermediate component 16. As in the illustrated embodiment, only a partial longitudinal length of the distal portion 12d of the proximal component 12 can be configured to be disposed within the intermediate component 16 such that only the internal stop surface 16i of the intermediate component 16 and the distal surface 12s of the proximal component 12 can be configured to cooperate as a stop mechanism. By being configured to allow only a partial portion of the reduced diameter region of the proximal portion 12 to be insertable into the intermediate component, the anchor 10 can be configured to provide a gap 22 between the proximal and intermediate components 12, 16 when the proximal component 12 is fully inserted into the intermediate component 16. The gap 22 can extend around a perimeter or circumference of the distal portion 12p of the proximal component 12. The gap 22 can help provide space for a suture coupled to the anchor 10 to be positioned outside the anchor 10, as discussed further below.

As mentioned above, the distal component 14 can also have a variety of sizes, shapes and configurations. As in the illustrated embodiment, the distal component 14 can taper distally to facilitate insertion of the distal component 14 within a bone hole and to facilitate receipt of the intermediate component 16 within the inner lumen 15 thereof. As in the illustrated embodiment, the distal component 14 can have a dome or bullet shape with a rounded end of the distal component 14 at a distal end thereof. A distal end of a distal component can, however, be configured as a penetrating tip, e.g., be tapered, pointed, and/or sharpened, which can facilitate formation of a bone hole and/or facilitate penetration of the suture anchor into bone. Such a suture anchor can therefore be configured to be self-awling or self-tapping in which a bone hole need not be pre-formed prior to inserting the suture anchor into bone. The distal component 14 can have an external surface free of bone-engaging surface features. Being free of external bone-engaging surface features can allow the distal component 14 to be freely slidable within a bone hole.

The distal component 14 can be cannulated, as mentioned above. The inner lumen 15 of the distal component 14 can include a proximal portion including a cavity 21 configured to receive the intermediate component 16 and a distal portion configured to threadably engage an instrument, e.g., a driver shaft, inserted therethrough. The proximal portion can have a larger diameter than the distal portion, as in the illustrated embodiment. The proximal portion of the inner lumen 15 can have a size configured to allow the intermediate component 16 to be received at least partially therein, as discussed further below.

The distal portion of the distal component's inner lumen 15 can include at least one internal thread 19 therein. The thread 19 can be a single, continuous thread as in the illustrated embodiment that extends around the inner lumen 15, or the thread 19 can include a plurality of threads, as will be appreciated by a person skilled in the art. In an exemplary embodiment, the internal thread 19 can be located in a distal portion of the inner lumen 15 of the distal component 14 and it can extend from an intermediate position within the inner lumen 15 and extend to a distal end thereof. In this way, the inner lumen of the anchor 10 can have a proximal, unthreaded region and a distal, threaded region. The internal thread 19 can facilitate insertion of the anchor 10 into a bone hole by allowing an instrument such as a driver to threadably engage the anchor 10 in a substantially fixed position during insertion of the anchor 10 into a bone hole. The internal thread 19 can also facilitate insertion of the intermediate component 16 into the distal component 14, e.g., into the cavity 21, by allowing the distal component 14 to be movable relative to the intermediate component 16. As discussed further below, an instrument such as a driver threadably engaged with the internal thread 19 can be moved proximally and/or distally to correspondingly move the distal component 14 proximally and/or distally relative to a remainder of the anchor 10, e.g., to the proximal and intermediate components 12, 16. When the instrument and the distal component 14 are moved together proximally relative to the proximal and intermediate components 12, 16, the intermediate component 16 can be received within the distal component's inner lumen 15.

The distal component 14 can be configured to selectively radially expand, such as by inserting the intermediate component 16 at least partially therein, e.g., by positioning at least a portion of the intermediate component 16 distally into the inner lumen 15 of the distal component 14. In an exemplary embodiment, a substantial portion of the intermediate component 16 can be received within the inner lumen 15 of the distal component 14. The anchor 10 can therefore be configured to be movable between a first, undeployed configuration, shown in FIG. 1, and a second, deployed configuration, shown in FIG. 2, in which the distal component 14 is radially expanded as compared to the distal component 14 in the first configuration. In this way, the distal component 14 can be configured to be slidably movable within a bone hole when the anchor 10 is disposed in the bone hole in the undeployed configuration, and to radially expand and press against a bone surface of the bone hole when the anchor 10 is disposed in the bone hole in the deployed configuration, thereby helping to prevent the anchor 10 from being removed therefrom. The anchor 10 can also be configured to engage the bone hole in a second, independent way. The anchor 10 can be configured to threadably engage the bone surface of the bone hole, e.g., with the threads 18 formed on the external surface of the proximal portion 12, thereby helping to retain the anchor 10 within the bone hole until the anchor 10 is manually removed or bio-absorbed.

The distal component 14 can be configured to receive any amount of the intermediate component 16. In an exemplary embodiment, a greater amount of the intermediate component 16 can be disposed within the distal component 14 when the anchor 10 is in the deployed configuration than when the anchor 10 is in the undeployed configuration. When the anchor 10 is in the deployed configuration, one or more holes or openings 24a, 24b of the intermediate component 16, discussed further below, can be contained within the distal component 14, as shown in FIG. 2, which can help compress one or more sutures between the distal and intermediate components 14, 16.

In an exemplary embodiment, the distal component 14 can be configured to radially expand such that it changes in height and in width. The anchor 10 can have a first longitudinal length L1 in the undeployed configuration and can have a second, smaller longitudinal length L2 in the deployed configuration. Similarly, the distal component 14 can have a first width W1 and a first height H1 when the anchor 10 is in the undeployed configuration and can have a second, larger width W2 and a second, smaller height H2 when the anchor 10 is in the deployed configuration. The first width W1 of the distal component 14 can be a maximum width of the distal component 14 in the anchor's undeployed configuration and can be equal to or less than a minimum outer width W3 of the proximal component 12. In this way, the distal component 14 can be configured to be slidably movable within a bone hole when the anchor 10 is disposed therein in the undeployed configuration to allow the anchor 10 to be disposed distally far enough into the bone hole to allow the threads 18 formed on the proximal component 12 to begin to engage the bone. Similarly, the second width W2 of the distal component 14 can be equal to or greater than the minimum outer width W3 of the proximal component 12. The distal component 14 can therefore be configured to press against a bone surface of the bone hole when the anchor 10 is disposed therein in the deployed configuration, thereby helping to prevent the anchor 10 from being removed therefrom. The anchor 10 can also be configured to help prevent the anchor 10 from being removed from the bone hole in a second, independent way. The anchor 10 can be configured to threadably engage the hone surface of the bone hole, e.g., with the threads 18 formed on the external surface of the proximal portion 12, thereby helping to retain the anchor 10 within. the hone hole until the anchor 10 is manually removed or bio-absorbed.

The intermediate component 16 can also have a variety of sizes, shapes, and configurations, and it can be cannulated, as mentioned above, and can have an external surface free of bone-engaging surface features. Being free of bone-engaging surface features can allow the intermediate component 16 to be freely slidable within a bone hole. The intermediate component 16 can taper distally to facilitate insertion of the intermediate component 16 within the inner lumen 15 of the distal component 14, e.g., within the cavity 21. As in the illustrated embodiment, the intermediate component 16 can have a dome or bullet shape with a tapered or rounded end of the intermediate component 16 being directed distally. At least a proximal portion of the inner lumen 15 of the distal component 14 can have a shape configured to receive at least a portion of the intermediate component 16, similar to a ball and socket joint in which the intermediate component 16, or ball, can be received within the distal component 14, or socket. The size of the intermediate component 16 can vary, but in an exemplary embodiment, the intermediate component 16 can have a maximum width W4 that is greater than a width W5 of the inner lumen 15 of the distal portion 14 in at least a proximal portion thereof, thereby allowing the intermediate component 16 to radially expand the distal component 14 as the intermediate component 16 is received in the inner lumen 15 of the distal component 14. In an exemplary embodiment, the maximum width W4 of the intermediate component 16 can be equal to the width of the distal component 14 when the anchor 10 is in the undeployed configuration, e.g., the width W4 can equal the first width W1, and can be less than the width of the distal component 14 when the anchor 10 is in the deployed configuration, e.g., the width W4 can be less than the second width W2.

The intermediate component 16 can include the one or more openings 24a, 24b formed therethrough, which can each be in communication with the inner lumen 17 of the intermediate component 16, and hence be in communication with the inner lumen of the anchor 10. Each of the one or more openings 24a, 24b can be located in an intermediate portion of the intermediate component 16 between proximal and distal ends of the intermediate component 16. In an exemplary embodiment, each of the openings 24a, 24b can be located distal to a distal end of the proximal component 12 when the proximal component 12 is fully received within the inner lumen 17 of the intermediate component 16. In other words, each of the openings 24a, 24b can be located distal to the internal stop surface 16i formed within the intermediate component 16. By being located distal to a distal position of the proximal component 12, the openings 24a, 24b can help ensure that any sutures passing therethrough pass through an entire longitudinal length of the proximal component 12, e.g., through an entire longitudinal length of the proximal component's inner lumen 13, which can help maximize an amount of the suture(s) that are engaged by the threads 18 and engaged between the distal and intermediate components 14, 16, as discussed further below.

One or more of the openings 24a, 24b can be configured as a tunnel extending all the way through the intermediate component 16 to pass through opposed sidewalls thereof, as both the openings 24a, 24b are in the illustrated embodiment. Additionally or alternatively, one or more of the openings 24a, 24b can be configured as a tunnel having one end passing through a sidewall of the intermediate component 16 and another end terminating at the inner lumen 17 of the intermediate component 16.

The one or more openings 24a, 24b can each be configured to receive at least one suture to allow the at least one suture to pass therethrough. The one or more openings 24a, 24b can thus be configured to allow a suture positioned within the inner lumen 17 of the intermediate portion 16, and hence within the inner lumen of the anchor 10, to exit the intermediate portion 16, and hence exit the anchor 10. In other words, the one or more openings 24a, 24b can each allow a suture coupled to the intermediate portion 16 to enter the inner lumen 17 of the intermediate component 16 through a proximal end thereof and to extend through a partial length of the inner lumen 17 of the intermediate portion 16 before exiting the intermediate portion 16, and hence exiting the inner lumen of the anchor 10, through the one or more openings 24, 24b, e.g., through a selected one of the openings 24a, 24b.

Although the intermediate component 16 in the illustrated embodiment includes two openings 24a, 24b, the intermediate component 16 can include one opening formed therethrough or a plurality of openings formed therethrough. Providing a plurality of openings through the intermediate component 16 can provide more options for positioning of a suture outside the anchor 10 by allowing the suture to be passed through a selected one of the plurality of openings. Providing a plurality of openings through the intermediate component 16 can allow each of the openings to accommodate one suture of a plurality of sutures coupled to the anchor 10. The number of openings formed through the intermediate component 16 can therefore equal a number of sutures coupled to the anchor 10. Although, the number of sutures coupled to the anchor 10 can be different than the number of openings, such as in the embodiment illustrated in FIGS. 1 and 2 where a number of openings 24, 24b, e.g., two, exceeds a number of sutures 20, e.g., one, coupled to the anchor 10. Additionally, even if an anchor includes a plurality of openings and has a plurality of sutures coupled thereto, each of the openings can have any number of sutures passing therethrough, e.g., zero, one, two, etc.

The anchor 10 can include a stop mechanism configured to prevent an elongate shaft, e.g., an insertion shaft of a driver, from being inserted distally through the anchor 10 beyond a certain amount. In an exemplary embodiment, the inner lumen 13 of the proximal component 12 can include a shaft stop surface 13s configured as such a stop mechanism.

The inner lumen of the anchor 10 can have different cross-sectional shapes along a longitudinal length thereof. The different cross-sectional shapes can help allow the proximal component 12 to be rotatable, e.g., about the longitudinal axis A of the anchor 10, relative to the distal and intermediate components 14, 16. Proximal to the shaft stop surface 13s, the inner lumen of the anchor 10 can have a first cross-sectional shape, and it can have a second, different cross-sectional shape distal to the stop surface 13s. The inner lumen 13 of the proximal component 12 can therefore have different cross-sectional shapes along a longitudinal length thereof. Although the first and second cross-sectional shapes can vary, in an exemplary embodiment, the first cross-sectional shape can be hexagonal, and the second cross-sectional shape can be circular.

As discussed further below, the anchor 10 can be configured to have one or more sutures 20 extending through at least a portion of the cannulated interior of the anchor 10. Although only one suture 20 is illustrated in FIGS. 1 and 2 as being coupled to the anchor 10, a plurality of sutures can be simultaneously coupled to the anchor 10. Additionally, the at least one suture 20 is shown in FIGS. 1 and 2 as a non-folded single strand, but any one or more sutures coupled to the anchor 10 can be folded any number of times, e.g., doubled over. Although the at least one suture 20 is shown passing through one of the openings 24b, the at least one suture 20 and/or any other sutures coupled to the anchor 10 can instead, as mentioned above, pass through the other opening 24a.

Whether the anchor 10 is in the undeployed or deployed configuration, the proximal portion 12 of the anchor 10 can be configured to compress the one or more sutures 20 between an external surface of the proximal portion 12 and a bone surface of a bone hole in which the anchor 10 is disposed, thereby helping to secure the one or more sutures 20, and hence any soft tissue attached thereto, in place relative to the bone hole. When the anchor 10 is in the undeployed configuration, the one or more sutures 20 can be configured to be freely movable or slidable through at least the distal and intermediate components 14, 16. When the anchor 10 is in the deployed configuration, the one or more sutures 20 can be configured to be in a locked or fixed position relative to at least the distal and intermediate components 14, 16. The anchor 10 can therefore be configured to help securely hold the one or more sutures 20, and hence any soft tissue attached thereto, in place relative to the bone hole in two independent ways: with a cooperative relationship between the proximal component 12 and the bone surface of the bone hole, and with a cooperative relationship between the distal and intermediate components 14, 16. The at least one suture 20 can therefore be less likely to slip or migrate after the suture anchor has been implanted into bone and soft tissue attached to the at least one suture 20 has been positioned relative to the bone.

A compression fit between the distal and intermediate components 14, 16 can help hold the anchor 10 in the deployed configuration. Additionally or alternatively, the anchor 10 can include a retention feature configured to hold the distal and intermediate components 14, 16 in a fixed position relative to one another when the anchor is in the deployed configuration, e.g., when the distal component is radially expanded. The retention feature can have a variety of sizes, shapes, and configurations. Exemplary embodiments of retention features include a snap lock and a protrusion and complementary depression, hole, or opening configured to receive the protrusion.

FIGS. 4 and 5 illustrate an exemplary embodiment of a suture anchor 100 that includes a retention feature. The anchor 100 can be configured similar to the anchor 10 of FIGS. 1-3 and can include a proximal component 112, a distal component 114, and an intermediate component 116 positioned between the proximal component 112 and the distal component 114. FIG. 4 illustrates the anchor 100 in an undeployed configuration, and FIG. 5 illustrates the anchor 100 in a deployed configuration in which the distal component 114 is radially expanded from its configuration when the anchor 100 is in the undeployed configuration.

As in this illustrated embodiment, the retention feature can be formed on the distal and intermediate components 114, 116 and can include a barb 101 at a distal end of the intermediate component 116 and a retention surface 103 formed within the inner lumen 115 of the distal component 114 that is configured to engage and retain the barb 101. The barb 101 can form a distal portion of the intermediate component 116, as in the illustrated embodiment. The barb 101 can include one or more retention hooks 105a, 105b extending proximally from a distal base 107 of the barb 101. Although the anchor 100 in this embodiment includes two retention hooks 105a, 105b, the anchor 100 can include any number of retention hooks. The barb 101 can be configured to be movable between a proximal, disengaged position when the anchor 100 is in the undeployed configuration and a distal, retained position when the anchor 100 is in the deployed configuration. The intermediate component 116 can be configured to move the barb 101 from the proximal position to the distal position by pushing the barb 101 distally as the intermediate component 116 is advanced distally into the inner lumen 115 of the distal component 114. When the intermediate component 116 has advanced a sufficient amount into the inner lumen 115, the retention hooks 105a, 105b can be configured to engage and hook the retention surface 103, thereby helping to retain the intermediate component 116 at least partially disposed within the distal component 114.

FIGS. 6 and 7 illustrate another exemplary embodiment of a suture anchor 200 that includes a retention feature. The anchor 200 can be configured similar to the anchor 10 of FIGS. 1-3 and the anchor 100 of FIGS. 4 and 5 and can include a proximal component 212, a distal component 214, and an intermediate component 216 positioned between the proximal component 212 and the distal component 214. FIG. 6 illustrates the anchor 200 in an undeployed configuration, and FIG. 7 illustrates the anchor 200 in a deployed configuration in which the distal component 214 is radially expanded from its configuration when the anchor 200 is in the undeployed configuration. FIG. 7 also illustrates an embodiment in which the intermediate component 216 of the anchor 200 can be disposed entirely within the distal component 214 when the distal component 214 is radially expanded therearound, e.g., when the anchor 200 is in the deployed configuration.

As in this illustrated embodiment, the retention feature can be formed on the proximal and distal components 212, 214 and can include one or more protrusions 201 formed on the distal component 214 that can be configured to engage corresponding depressions 203 formed on the proximal component 212. Although the anchor 200 in this embodiment includes two protrusions 201 and two depressions 203, the anchor 200 can include any number of protrusions and depressions.

Figure 9:
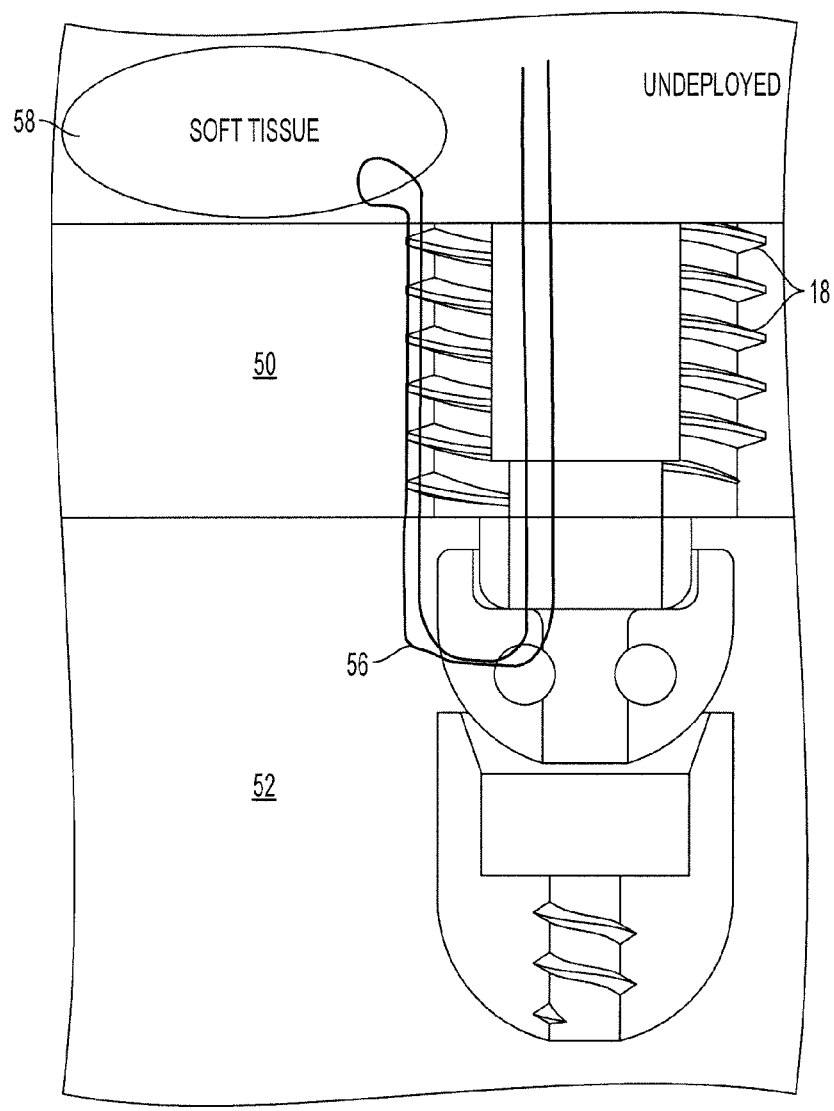
FIG. 9 is a side, cross-sectional view of the suture anchor of FIG. 8 further disposed in the undeployed configuration in the bone hole.
Figure 10:
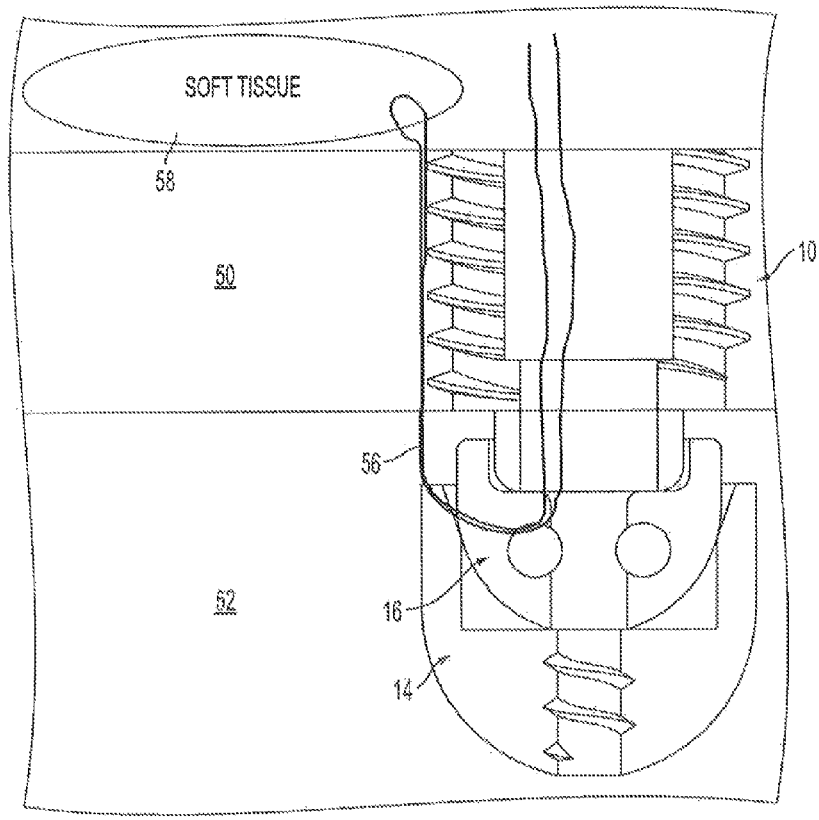
FIG. 10 is a side, cross-sectional view of the suture anchor of FIG. 9 disposed in the deployed configuration in the bone hole.

As mentioned above, the suture anchors discussed herein can be used to anchor soft tissue to bone. While the following method is described in connection with attaching soft tissue to bone, the methods and devices disclosed herein can be used in a variety of medical procedures for anchoring one structure to another. Additionally, although the following exemplary method for securing soft tissue to bone illustrated in FIGS. 8-10 is discussed with reference to the suture anchor 10 of FIGS. 1-3, any of the suture anchors and disclosed herein can be similarly used to anchor one structure to another, e.g., soft tissue to bone.

To attach soft tissue to bone, a bore, bone hole, or bone tunnel can be formed in bone of a patient. The bone hole can be pre-formed, such as by using a drill, an awl, a punch instrument, etc., as will be appreciated by a person skilled in the art. Alternatively, the bone hole can be formed simultaneously with advancement of a suture anchor into bone and simultaneously with threadable engagement of the anchor therewith, such as by using a self-awling or self-tapping driver and/or self-awling or self-tapping anchor. A diameter of the bone hole can vary. In an exemplary embodiment, it can be slightly less than a maximum outer diameter W6 of the anchor 10 and be substantially equal to the minimum outer width W3 of the proximal component 12, to be disposed within the bone hole, and a length of the bone hole can be the same as or slightly greater than a length of the anchor 10. The bone hole can extend fully through cortical bone 50 to allow the suture anchor to be fully engaged through the thickness of the cortical bone 50. The bone hole 50 can also extend into cancellous bone 52 located underneath the cortical bone 50.

As shown in FIG. 8, the anchor 10 in the undeployed configuration, without the distal component 14 being radially expanded, can have one or more sutures 56 coupled thereto by extending at least partially through the inner lumen thereof. The one or more sutures 56 can be coupled to the anchor 10 before or after the bone hole is formed in the bone. Although the suture 56 is shown passing through one of the openings 24b, the suture 56 and/or any other sutures coupled to the anchor 10 can instead, as mentioned above, pass through the other opening 24a. In an exemplary embodiment, the suture 56 can be coupled to the anchor 10 after the bone hole 50 is formed. A soft tissue 58 can be coupled to the suture 56, e.g., by passing the suture 56 through the soft tissue 58, before or after the suture 56 is coupled to the anchor 10, but in an exemplary embodiment, the suture 56 can be coupled to the soft tissue 58 prior to the suture 56 being passed into the inner lumen of the anchor 10. Although only one suture 56 is illustrated in FIGS. 8-10 as being coupled to the anchor 10 and to the soft tissue 58, as mentioned above, a plurality of sutures can be simultaneously coupled to the anchor 10. Additionally, the suture 56 is shown in FIGS. 8-10 as being a double-folded single strand, but any one or more sutures coupled to the anchor 10 can be folded any number of times, e.g., doubled over.

The suture 56 can be passed into the anchor 10 through a proximal end thereof, e.g., through the proximal end of the proximal component 12, and through one of the openings 24a, 24b formed through the intermediate component 16 to exit the anchor 10. The suture 56 can therefore be loaded onto the anchor 10 to position a first length of the suture 56 within the inner lumen of the anchor 10, e.g., within the inner lumens 13, 17 of the proximal and intermediate components 12, 16, and to position a second length of the suture 56 external to the anchor 10 such that the second length can be positioned adjacent to the threaded external surface of the proximal component 12.

The suture 56 can be coupled to the anchor 10 before or after an instrument (not shown) configured to advance the anchor 10 into bone is inserted through the inner lumen of the anchor 10. In an exemplary embodiment, the anchor 10 can be pre-loaded onto a distal end of the instrument with the suture 56 coupled to the anchor 10 and to the instrument, such as by extending into an inner lumen thereof. Generally, the instrument can include an elongate insertion shaft configured to be advanced through the inner lumen of the anchor 10 such that the instrument threadably engages the internal thread 19 in the distal component 14 and a distal tip of the instrument extends distally beyond the anchor 10, e.g., passes outside the anchor 10 through the distal end of the distal component's inner lumen 15.

Figure 11:
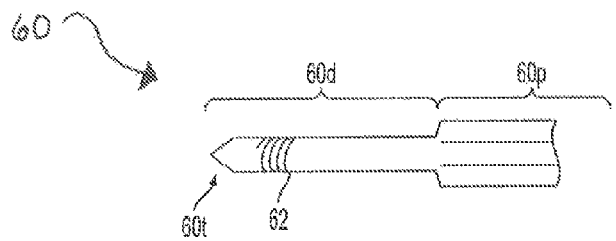
FIG. 11 is side, partial view of a distal portion of a suture anchor driver.

FIG. 11 illustrates an exemplary embodiment of an instrument configured to advance the anchor 10 into bone in the form of a driver 60. The driver 60 can include an elongate insertion shaft having a shape corresponding to the inner lumen of the anchor 10. The shaft can therefore have different cross-sectional shapes along a longitudinal length thereof. As in the illustrated embodiment, a proximal portion 60p of the shaft can have a first cross-sectional shape, e.g., hexagonal, and a distal portion 60d of the shaft can have a second cross-sectional shape, e.g., circular. The proximal portion 60p of the shaft can be configured to be positioned in the inner lumen 13 of the proximal component 12 and abut the shaft stop surface 13s such that the proximal portion 60p of the shaft can be located entirely proximal to the distal and intermediate components 12, 16. The distal portion 60d of the shaft can be configured to be positioned in the inner lumens 13, 15, 17 of the proximal, distal, and intermediate components 12, 14, 16 such that a distal tip 60t of the shaft extends distally beyond the anchor 10. The distal portion 60d can include an external thread 62 configured to threadably engage the internal thread 19 of the distal component's inner lumen 15 to threadably engage the anchor 10 and hold the shaft in a substantially fixed axial position relative thereto during insertion of the anchor 10 into the bone hole.

The distal tip 60t of the driver 60 can be configured as a penetrating tip, e.g., be tapered, pointed, and/or sharpened, which can facilitate formation of a bone hole and/or facilitate penetration of the shaft, and hence a suture anchor coupled thereto, into bone. The driver 60 can therefore be configured to be self-awling or self-tapping in which a bone hole need not be pre-formed prior to inserting the driver shaft, and a suture anchor coupled thereto, into bone. In this illustrated embodiment, the distal tip 60t is tapered, pointed, and sharpened. As mentioned above, a suture anchor can be configured as self-awling or self-tapping, and when such an anchor is used with a self-awling or self-tapping driver, can further facilitate insertion of the driver and the anchor into bone.

In an exemplary embodiment, the anchor 10 can be pre-loaded onto the elongate shaft of the driver with the suture 56 coupled to the anchor 10 and the driver. The suture 56 can extend within the inner lumen of the anchor 10, e.g., within the proximal component's inner lumen 13 and the intermediate component's inner lumen 17, along an external surface of the driver, and/or the suture 56 can extend within an inner passageway (not shown) of the driver. In an exemplary embodiment, the suture 56 can be located external to the driver at least within the anchor 10, which can facilitate removal of the driver from within the anchor 10 without unintentionally damaging or repositioning the suture 56 and the soft tissue 58 attached thereto.

The anchor 10 having the driver extending therethrough can be advanced distally into bone such that the anchor 10 is in a pre-threaded, undeployed configuration in which a distal portion of the anchor 10 is disposed within a bone hole formed in the bone without the anchor's external thread 18 engaging the bone, as shown in FIG. 8. The anchor 10 can be advanced distally into the bone to be in the pre-threaded, undeployed configuration by pushing the anchor 10 in a distal direction without rotating the anchor 10 because the external surfaces of the distal and intermediate components 14, 16 lack bone engaging-surface features and can slide within the bone hole. The anchor 10 can be advanced into the bone until just before the external thread 18 begins to engage the cortical bone 50, e.g., until the distal surface 12m of the proximal portion 12p abuts a proximal surface 50p of the cortical bone 50, as also shown in FIG. 8. The distal and intermediate components 14, 16 can therefore be disposed within the cortical bone 50 and/or cancellous bone 52 distal to the proximal surface 50p of the cortical bone 50. Depending on a particular patient's anatomy and the sizes of the distal and intermediate components 14, 16, when the anchor 10 is in the pre-threaded, undeployed configuration, the intermediate component 16 can be disposed entirely within the cortical bone 50, and at least a portion of the distal component 14 can be disposed within the cancellous bone 52.

When the anchor 10 is in the pre-threaded, undeployed configuration, a portion of the suture 56 can pass through the opening 24b and can be positioned external to the anchor 10. In this way, as shown in FIG. 9, when the anchor 10 is advanced distally to move from the pre-threaded, undeployed configuration to a threaded, undeployed configuration, shown in FIG. 9, the external thread 18 can engage the bone, and the suture 56 can be compressed between the bone surface of the bone hole and an external surface of the anchor 10, e.g., between the bone wall and the external surface of the proximal portion 12 of the anchor 10.

Prior to threadably engaging the anchor 10 with the bone, the suture 56 and the soft tissue 58 can be tensioned to position the soft tissue 58 to an optimal position relative to the bone. The suture 56 and the soft tissue 58 can be tensioned by pulling the suture 56 by hand and/or by tool. As the anchor 10 is threaded into the bone, the tension can be maintained by hand and/or by tool, e.g., by engaging the suture 56 onto a suture-retaining member (not shown) formed on the shaft of the driver. The suture-retaining member can have a variety of configurations, such as a compression-fit groove, a clip, a clamp, a post, an adhesive, etc.

The driver can be rotated about a longitudinal axis thereof, which can be the same axis as the anchor's longitudinal axis A, to drive the proximal portion 12 of the anchor 10 into the bone. As mentioned above, the different cross-sectional shapes of the anchor's inner lumen and corresponding different cross-sectional shapes of the driver's shaft can allow the proximal portion 12 of the anchor 10 to be rotated relative to the distal and intermediate components 14, 16. The suture 56 and the soft tissue 58 can therefore remain in substantially the same position as the anchor 10 is threaded into the bone. The helices of the external thread 18 and the internal thread 19 can rotate in opposite directions, e.g., one clockwise and the other counterclockwise. In this way, rotating the driver to rotate the proximal portion 12 into the bone can rotate the proximal portion 12 relative to the distal and intermediate components 14, 16 without unthreading the shaft thread 54 from the distal component's internal thread 19.

The anchor 10 can be inserted any depth into the bone, such as substantially flush or sub-flush with a proximal end of the bone hole. The shaft can have one or more depth markings (not shown) printed or otherwise formed on an external surface thereof. The depth marking(s) can be configured to facilitate visual assessment of the shaft's location within a body of a patient. In an exemplary embodiment, the shaft can include a distal depth marking such as a line around a perimeter of the shaft. The distal depth marking can help visually indicate when the anchor 10 has been inserted substantially flush or sub-flush with the proximal end of the bone hole. In an exemplary embodiment, the driver can be rotated until the distal depth marking is substantially flush with the proximal end of the bone hole, thereby indicating that the suture anchor 10 has been inserted substantially sub-flush into the bone hole with the thread 18 engaging the cortical bone 50, as shown in FIG. 9. The suture 56 can therefore be compressed between the anchor 10 and the cortical bone 50 along an entire longitudinal length of the proximal component 12. As also shown in FIG. 9, the anchor 10 can be in the undeployed configuration with the proximal component 12 positioned entirely within the cortical bone 50 and with the distal and intermediate 14, 16 components positioned entirely below the cortical bone 50, e.g., entirely within the cancellous bone 52. The proximal component 12 can, however, be at least partially disposed within the cancellous bone 52.

With the anchor 10 threadably engaging the bone, the suture 56 can be compressed between the bone and anchor 10 to help hold the suture 56 and the soft tissue 58 in a fixed position relative to the bone. As mentioned above, the suture 56 can also be compressed between the distal and intermediate components 14, 16 to further help hold the suture 56 and the soft tissue 58 in a fixed position relative to the bone. As also mentioned above, the distal component 14 can be configured to move relative to the intermediate component 16 to compress the suture 56 therebetween. In an exemplary embodiment, the driver can be pulled proximally to move the distal component 14 proximally relative to the intermediate component 16, as well as relative to the proximal component 12, to radially expand the distal component 14 as the intermediate component 16 is advanced therein. The anchor 10 can therefore be moved from the undeployed configuration to the deployed configuration, as shown in FIG. 10. The driver can be pulled proximally such that it can be moved without rotation to pull the distal component 14 proximally, which can help prevent the driver from becoming threadably disengaged from the distal component 14.

Once the distal component 14 is advanced over the intermediate component 16, the driver can be rotated, e.g., about a longitudinal axis thereof and/or about the longitudinal axis A of the anchor, to threadably disengage the driver from the internal thread 19 of the distal component 14. The driver can then be removed from the inner lumen of the anchor 10, e.g., by sliding the driver out of the anchor 10. Excess trailing ends of the suture 56 extending proximally from the bone hole can trimmed and, optionally, be secured together.

FIGS. 12-16 illustrate another exemplary embodiment of a method for securing soft tissue to bone, described with reference to the anchor 100 of FIGS. 4 and 5. For clarity of illustration, suture 156 coupled to the anchor 100 is not shown with any soft tissue attached thereto, and the suture 156 is omitted from FIGS. 13 and 15.

Figure 12:
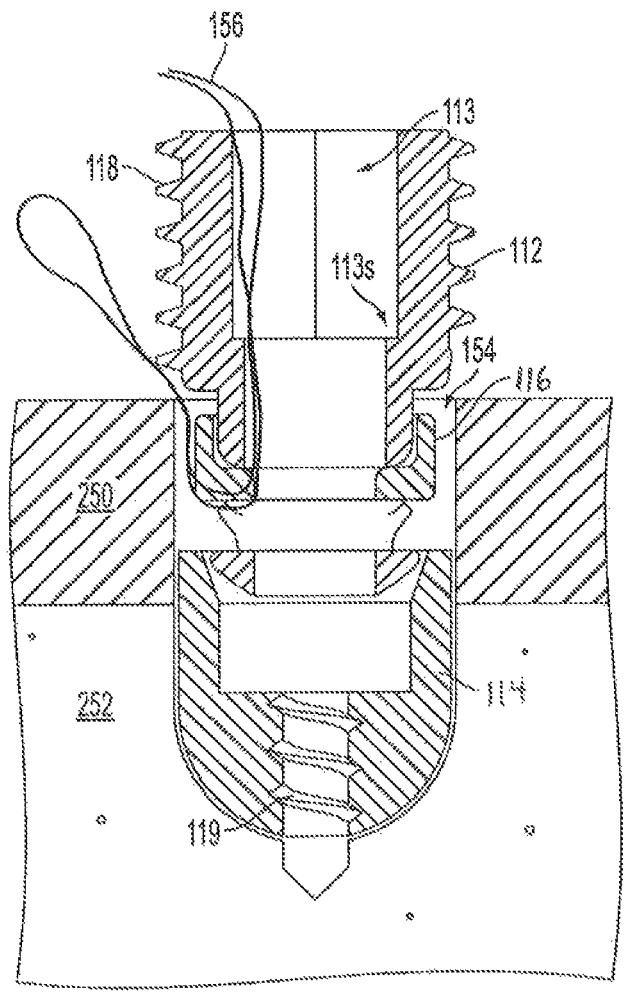
FIG. 12 is a side, cross-sectional view of the suture anchor of FIG. 4 partially disposed in the undeployed configuration in a bone hole.
Figure 13:
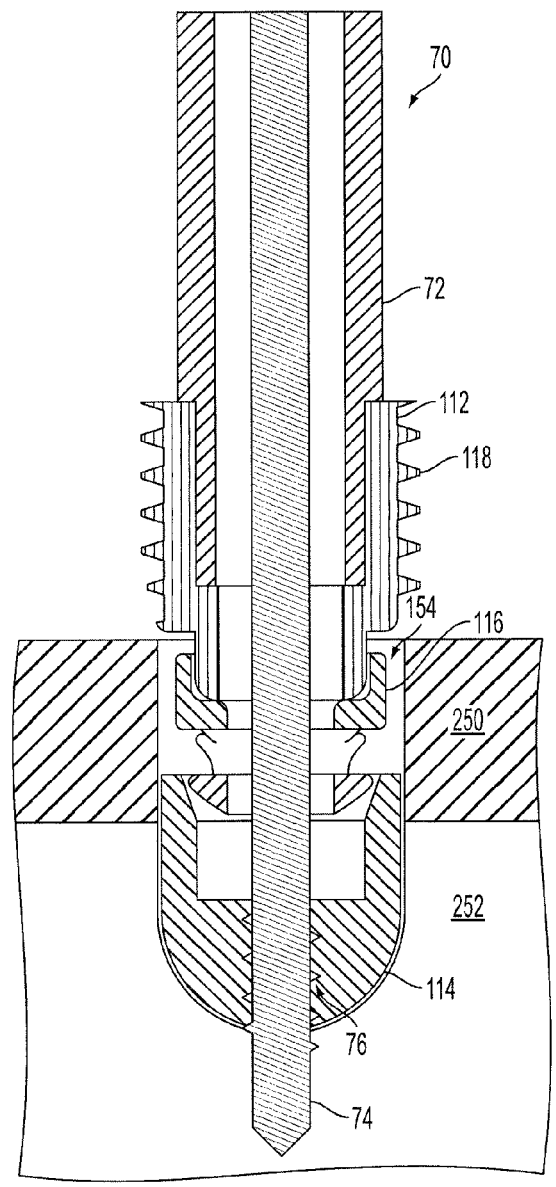
FIG. 13 is a side, cross-sectional view of the suture anchor of FIG. 11 having a suture anchor driver inserted therethrough.

The anchor 100 can be advanced into cortical bone 250 and/or cancellous bone 252 similar to that discussed above regarding FIGS. 8-10 in which the anchor 10 is implanted in bone. FIG. 12 illustrates the anchor 100 in a pre-threaded, undeployed configuration in which the distal and intermediate components 114, 116 have been driven into a bone hole 154 before an external thread 118 formed on the proximal component 112 engages the bone. FIG. 13 illustrates the anchor 100 in the pre-threaded, undeployed configuration with an exemplary embodiment of a driver 70 inserted through the inner lumen of the anchor 100.

The driver 70 can include an outer driver shaft 72 and an inner deployment shaft 74. The inner deployment shaft 74 can including a penetrating tip, as in the illustrated embodiment, to facilitate penetration of the driver 70 into bone. The outer driver shaft 72 can have a first cross-sectional shape, e.g., hexagonal, corresponding to a first cross-sectional shape, e.g., hexagonal, of the anchor's inner lumen. The outer driver shaft 72 can therefore be configured to abut a shaft stop surface 113s within an inner lumen 113 of the proximal component 112. The inner deployment shaft 74 can have a second cross-sectional shape, e.g., circular, corresponding to a second cross-sectional shape, e.g., circular, of the anchor's inner lumen. The inner deployment shaft 74 can include an external thread 76 configured to threadably engage an internal thread 119 formed in the distal component 114. The outer deployment shaft 72 can be configured to rotate independent of the inner deployment shaft 74, which can facilitate threading of the proximal component 112 into bone without disengaging the internal thread 119 from the inner deployment shaft's thread 76. The shaft threads 76, 119 can therefore have helices rotating in the same direction. Alternatively, the outer deployment shaft 72 can be configured to rotate with of the inner deployment shaft 74, in which case the shaft threads 76, 119 can have helices rotating in opposite directions.

Figure 14:
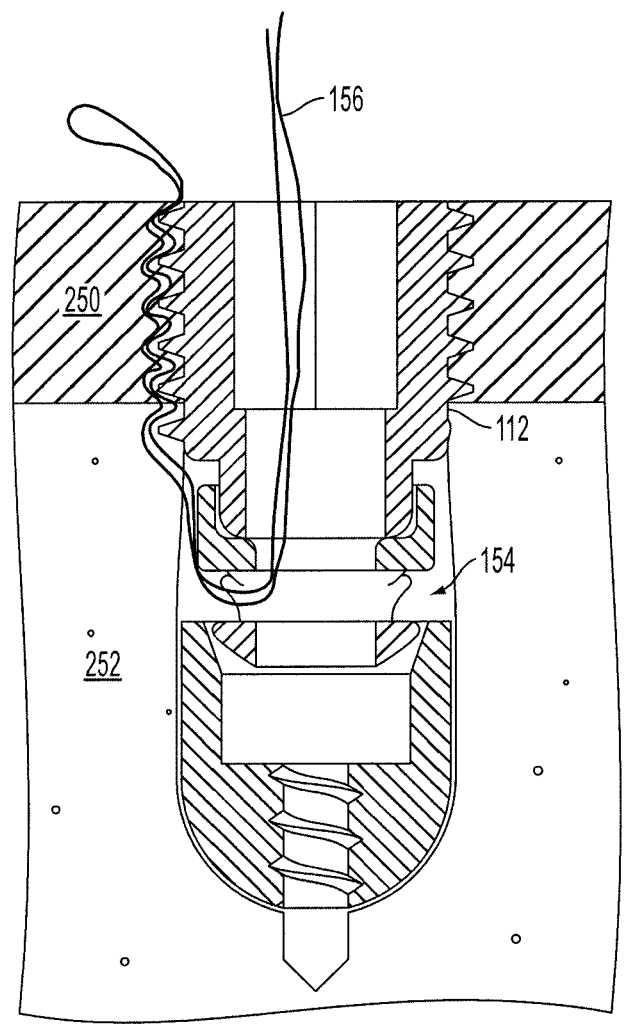
FIG. 14 is a side, cross-sectional view of the suture anchor of FIG. 12 further disposed in the undeployed configuration in the bone hole.
Figure 15:
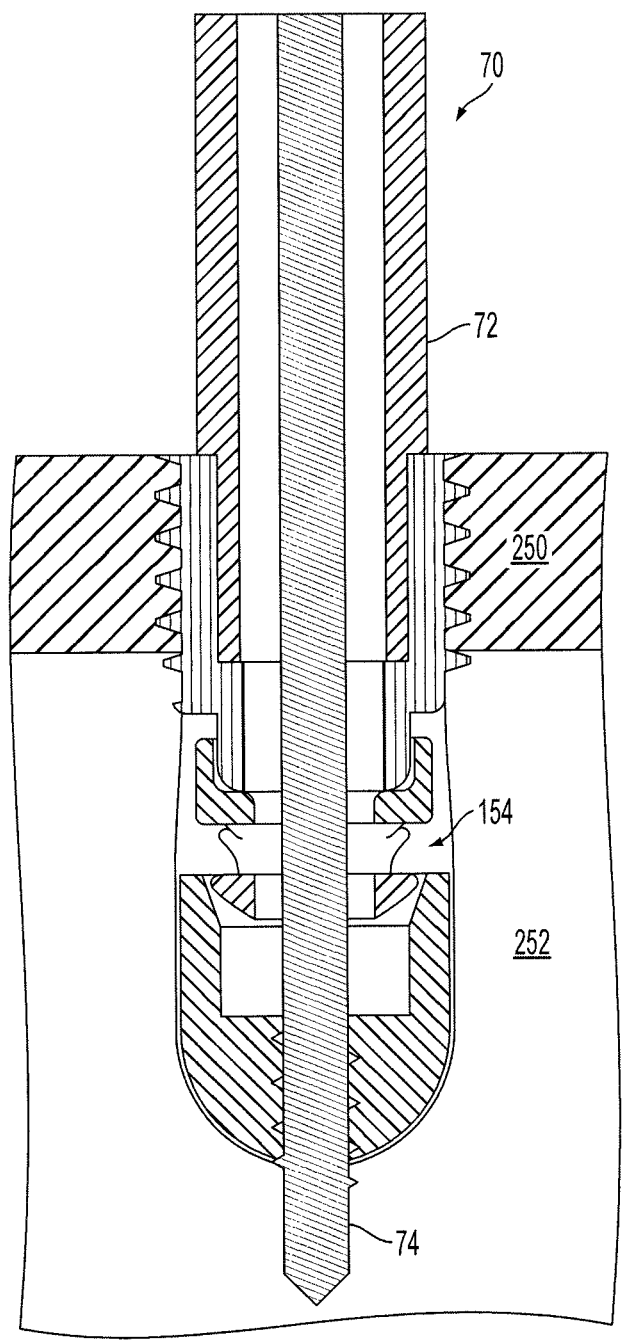
FIG. 15 is a side, cross-sectional view of the suture anchor of FIG. 14 having the suture anchor driver of FIG. 13 inserted therethrough.

FIG. 14 illustrates the anchor 100 moved from the pre-threaded, undeployed configuration to a threaded, undeployed configuration in which the proximal component 112 is threadably engaged with the bone and is disposed at least partially within the cortical bone 250. As in the illustrated embodiment, the proximal component 112 can be substantially flush or sub-flush with a proximal end of the bone tunnel 154 and can extend distally beyond the cortical bone 250 to be partially located in the cancellous bone 250. FIG. 15 illustrates the anchor 100 in the threaded, undeployed configuration with the driver 70 inserted through the inner lumen of the anchor 100.

Figure 16:
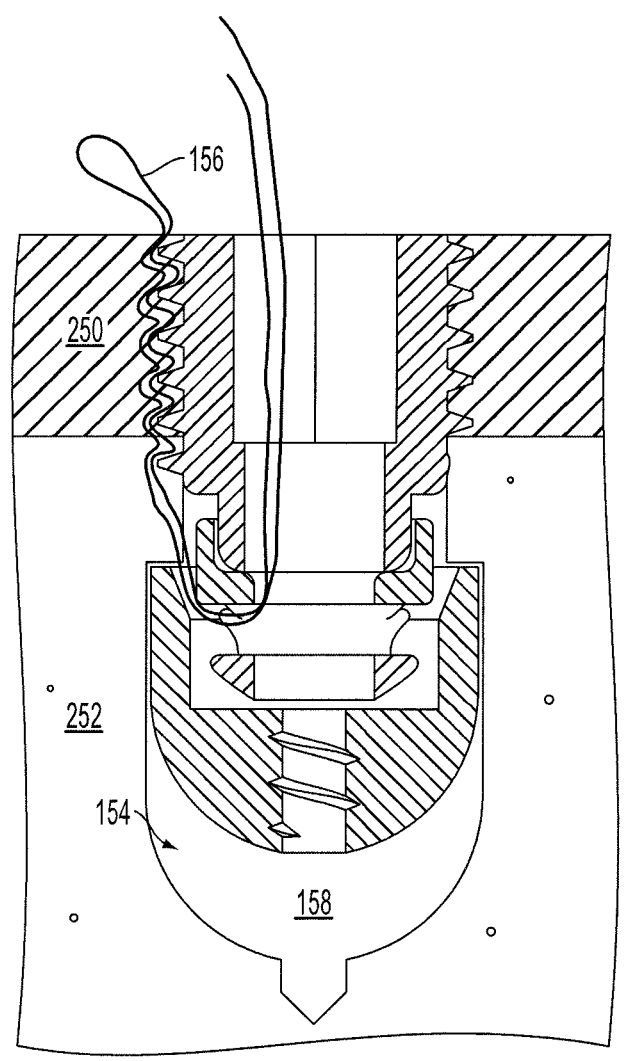
FIG. 16 is a side, cross-sectional view of the suture anchor of FIG. 14 disposed in the deployed configuration in the bone hole.

The anchor 100 can be moved from the threaded, undeployed configuration to a deployed configuration by moving the driver 70 proximally to radially expand the distal component 114. FIG. 16 illustrates the anchor 100 in the deployed configuration with the driver 70 removed therefrom. As shown in FIG. 16, when the intermediate component 116 has been advanced into the distal component 114, a gap or open space 158 previously occupied by the distal component 114 within the bone hole 154 can be formed at a distal end of the bone hole 154. As with any of the suture anchor discussed herein, a material can be injected or otherwise inserted through the inner lumen of the anchor 100 and into the open space 158. The material can be configured to further help retain the anchor 100 within the bone hole 154 and/or further facilitate healing. The material can be, for example, a bone-growth promoting material, a sealant, an adhesive, and combinations thereof. The trailing ends of the suture 156 extending proximally from the bone hole can be secured together and the excess trimmed.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A suture anchor, comprising:
a cannulated elongate member comprising a distal component, a proximal component, and an intermediate component positioned between the distal component and the proximal component, the distal, proximal, and intermediate components each being configured to move independent of one another, the proximal component being configured to be at least partially inserted into the intermediate component, the cannulated elongate member being configured to be secured within a bone hole by a threaded engagement between the proximal component and the bone hole, and by radial expansion of the distal component within the bone hole such that at least a portion of the radially expanded distal component directly contacts bone within the bone hole, and the cannulated elongate member being configured to secure a suture thereto by engaging the suture between the bone hole and threads formed on an external surface of the proximal component, and by engaging the suture between the distal component and the intermediate component.

2. The suture anchor of claim 1, wherein the proximal, intermediate, and distal components are axially aligned.

3. The suture anchor of claim 1, wherein the proximal component is configured to rotate about a longitudinal axis thereof relative to the intermediate and distal components.

4. The suture anchor of claim 1, wherein the distal component is configured to radially expand and engage the suture between the distal component and the intermediate component when the intermediate component is inserted into a bore formed in the distal component.

5. The suture anchor of claim 1, wherein the intermediate component has a hole formed through a sidewall thereof proximal to a distal end of the intermediate component and proximal to a proximal end of the distal component, the hole being configured to have the suture extend therethrough at least when the suture is engaged between the distal component and the intermediate component.

6. The suture anchor of claim 1, wherein the intermediate and distal components have unthreaded external surfaces.

7. A suture anchor, comprising:
a cannulated elongate member comprising a distal component, a proximal component, and an intermediate component positioned between the distal component and the proximal component;
wherein, when the cannulated elongate member is disposed within a bone hole and a suture is coupled to the cannulated elongate member, the cannulated elongate member is configured to have a first configuration in which the proximal component is threadably engaged with the bone hole to prevent removal of the cannulated elongate member from the bone hole, and the suture is engaged between the bone hole and threads on an external surface of the proximal component, the suture being freely slidable through the intermediate component, and a second configuration in which the distal component is advanced proximally over the intermediate component without advancing over the threads of the proximal component such that the distal component radially expands, as compared to the distal component in the first configuration, to engage the bone hole, and the suture is engaged between the distal component and the intermediate component.

8. The suture anchor of claim 7, wherein when the cannulated elongate member is in the second configuration, the proximal component is threadably engaged with the bone hole to prevent removal of the cannulated elongate member from the bone hole.

9. The suture anchor of claim 7, wherein when the cannulated elongate member is in the second configuration, the suture is not freely slidable through the intermediate component.

10. The suture anchor of claim 7, wherein when the cannulated elongate member is in the first configuration, a first length of the intermediate component is disposed within the distal component, and when the cannulated elongate member is in the second configuration, a second length of the intermediate component is disposed within the distal component, the second length being greater than the first length.

11. The suture anchor of claim 7, wherein the distal component in the first configuration has a first height that is different from a second height of the distal component in the second configuration.

12. The suture anchor of claim 7, wherein, in the first and second configurations, a distal portion of the proximal component is positioned in an inner lumen of the intermediate component and a distal portion of the intermediate component is positioned in an inner lumen of the distal component.

13. A suture anchoring system, comprising:
an elongate shaft having a proximal handle portion and a distal portion configured to be inserted through tissue;
a proximal component freely slidably disposed on the distal portion of the elongate shaft and having threads formed on an external surface thereof;
an intermediate component freely slidably disposed on the distal portion of the elongate shaft at a location distal to the proximal component with a distal portion of the proximal component disposed within the intermediate component; and
a distal component threadably engaged with threads formed on the distal portion of the elongate shaft, the distal component being positioned distal to the intermediate component with a distal portion of the intermediate component disposed within the distal component, and the distal component being configured to expand when the distal component is advanced over the intermediate component.

14. The system of claim 13, wherein the distal and intermediate components are configured to engage a suture therebetween when the distal component is advanced over the intermediate component.

15. The system of claim 13, wherein the elongate shaft is configured to move proximally relative to the proximal and intermediate components to advance the distal component proximally relative to the proximal and intermediate components such that the distal component expands around the intermediate component.

16. The system of claim 15, wherein the elongate shaft is configured to be threadably disengaged from the distal component after the distal component has radially expanded around the intermediate component to allow the elongate shaft to be slidably released from the proximal, intermediate, and distal components.

17. The system of claim 13, wherein the elongate shaft extends through axially aligned inner lumens formed through the proximal, intermediate, and distal components.

18. A method for anchoring tissue to bone, comprising:
advancing a suture anchor disposed on a distal end of an insertion shaft into bone distally such that the suture anchor is at least partially disposed within the bone, threads on a proximal portion of the suture anchor are engaged with the bone, and a suture coupled to soft tissue is engaged between an outer surface of the suture anchor and the bone; and
after advancing the suture anchor into the bone, moving a sleeve of the suture anchor located distal to the proximal portion proximally, without advancing over the threads on the proximal portion of the suture anchor, to cause the sleeve of the suture anchor to expand to engage the bone and prevent removal of the suture anchor from the bone, and to cause the suture to be engaged by compression fit between the sleeve and a pin member of the suture anchor.

19. The method of claim 18, wherein the insertion shaft comprises a bone-penetrating distal tip, and advancing the suture anchor comprises forming a hole in the bone.

20. The method of claim 18, wherein advancing the suture anchor comprises positioning the suture anchor into a preformed hole in the bone.

21. The method of claim 18, wherein advancing the suture anchor comprises rotating the insertion shaft and the proximal portion of the suture anchor relative to the pin member and the sleeve.

22. The method of claim 18, wherein actuating the suture anchor comprises advancing the insertion shaft proximally such that the sleeve moves proximally relative to the pin member and the proximal portion of the suture anchor.

23. The method of claim 22, wherein advancing the insertion shaft proximally comprises pulling the insertion shaft in a proximal direction.

24. The method of claim 18, wherein when the suture anchor is advanced into the bone and when the suture anchor is actuated, the insertion shaft extends through axially aligned inner lumens formed through the proximal portion, the sleeve, and the pin member, the pin member being located between the sleeve and the proximal portion.

25. A suture anchor, comprising:
a cannulated elongate member comprising a distal component, a proximal component, and an intermediate component positioned between the distal component and the proximal component, the distal, proximal, and intermediate components each being configured to move independent of one another, the cannulated elongate member being configured to be secured within a bone hole by a threaded engagement between the proximal component and the bone hole, and by radial expansion of the distal component within the bone hole such that at least a portion of the radially expanded distal component directly contacts bone within the bone hole, and the cannulated elongate member being configured to secure a suture thereto by engaging the suture between the bone hole and threads formed on an external surface of the proximal component, and by engaging the suture between the distal component and the intermediate component, wherein the intermediate component has a hole formed through a sidewall thereof proximal to a distal end of the intermediate component and proximal to a proximal end of the distal component, the hole being configured to have the suture extend therethrough at least when the suture is engaged between the distal component and the intermediate component.

* * * * *